United States Patent [19]
Darteil et al.

[11] Patent Number: 6,080,850
[45] Date of Patent: Jun. 27, 2000

[54] FELINE INFECTIOUS PERITONITIS VACCINE

[75] Inventors: Raphaël Darteil, Lyons, France; Wayne Corapi, Staten Island, N.Y.; Franqis Jean-Christophe Audonnet; Emile Gilles Chappuis, both of Lyons, France

[73] Assignee: Rhone Merieux, France

[21] Appl. No.: 08/519,979

[22] Filed: Aug. 28, 1995

[30] Foreign Application Priority Data

Aug. 29, 1994 [FR] France ................................. 94 10379

[51] Int. Cl.[7] .............................. C07H 21/04; C07K 1/00
[52] U.S. Cl. ......................................... 536/23.72; 530/350
[58] Field of Search .............................. 424/186.1, 199.1, 424/221.1, 205.1; 435/69.3, 172.3, 235.1, 320.1, 252.3, 236; 536/23.72; 935/9, 12, 65; 530/350

[56] References Cited

FOREIGN PATENT DOCUMENTS

| | | |
|---|---|---|
| 0 264 979 | 4/1988 | European Pat. Off. . |
| 91/08525 | 6/1992 | WIPO . |
| 93/23422 | 11/1993 | WIPO . |
| 94/10634 | 3/1995 | WIPO . |
| 95/07987 | 3/1995 | WIPO . |

OTHER PUBLICATIONS

Jacobs et al. "The nucleotide sequence of the peplomer gene of porcine transmiccible gastroenteritis (TGEV): comparison with the sequence of the peplomer protein of feline infectious peritonitis virus (FIPV)". Virus Research. vol. 8:363–371, 1987.

Correa et al. "Localization of antigenic sites of the E2 glycoprotein of transmissible gastroenteritis coronavirus". Journal of General Virology. vol. 71:271–279, 1990.

Ellis et al. "New Technologies for Making Vaccines". Vaccines. Plotkin et al., Eds. Chapter 29. pp. 568–575, 1988.

Monoclonal Antibodies to the Spike Protein of Feline Infectious Peritonitis Virus Mediate Antibody–Dependent Enhancement of Infection of Feline Macrophages; Journal of Virology, Feb. 1992, vol. 66, No. 2, P 956–965.

Early Death after Feline Peritonitis Virus Challenge due to Recombinant Vaccinia Virus Immunization; Journal of Virology, Mar. 1990; vol. 63, No. 3 p. 1407–1409.

Journal of General Virology, vol. 74, 1993 Reading, GB, pp. 745–749; Olsen C. et al; "Identification of antigenic sited mediating antibody–dependent enhancement of feline infectious peritonitis viris infectivity".

Journal of Virology, vol. 66 No. 11, Nov. 1992, pp. 6695–6705; Corapi, W. et al; "Monoclonal antibody analysis of neurtralization and antibody–dependent enhancement of feline infectious peritonitis virus".

Journal of General Virology, vol. 68, No. 10, Oct. 1987; Reading, GB, pp. 2639–2646, De Groot, R. et al; "cDNA cloning and sequence analysis of the gene encoding the peplomer protein of feline infectious peritonitis virus".

Journal Of Virology, vol. 69, No. 5, May 1995; pp. 2858–2862; Corapi. W. et al; "Localization of antigenic sites of the S glycoprotein of feline infectious peritonitis virus involved in neutralization and antibody–dependant enhancement".

*Primary Examiner*—Paula K. Hutzell
*Assistant Examiner*—Brenda G. Brumback
*Attorney, Agent, or Firm*—Larson & Taylor PLC

[57] ABSTRACT

The invention comprises the nucleotide sequences comprising the FIPV S gene, or a fragment of this gene, which are modified in at least one of the antigenic regions A1 and A2 which are involved in enhancement, as well as the use of these sequences for the expression of modified proteins, and for the construction of recombinant viruses or expression plasmids, and the use of the recombinant viruses as vaccines against feline infectious peritonitis, the use of the expression plasmids as immunizing composition by direct injection of the said plasmids into cats, and the use of the modified proteins as vaccine.

8 Claims, No Drawings

FELINE INFECTIOUS PERITONITIS VACCINE

1. Field of the Invention

The present invention relates to vaccines against Feline Infectious Peritonitis (FIP) prepared from the SPIKE (S) glycoprotein from the FIP virus whose major enhancing epitopes have been modified by mutagenesis.

These vaccines allow protection of cats vaccinated against FIP without causing in them the enhancement phenomenon which leads to an accelerated progression of the disease.

2. Prior State of the Art

The Feline Infectious Peritonitis Virus (FIPV) is an enveloped, positive single-stranded RNA virus which, within the Coronaviridae family, belongs to the antigenic is group which comprises the enteric feline coronavirus (FECV), the canine coronavirus (CCV), the pork transmissible gastroenteritis virus (TGEV) and the porcine respiratory coronavirus (PRCV) (Sanchez C. et al. Virology, 1990, 174, 410–417). This virus causes a disease which is complex and always fatal in cats, known as Feline Infectious Peritonitis (FIP). The FIP virus is defined among coronaviruses because it induces in cats the appearance of antibodies which enhance the infection by the virus and accelerate the progression of the disease. Cats having anti-FIPV neutralizing antibodies following a previous natural infection with this virus, following a passive transfer of antibody or following a vaccination, very frequently develop a disease which is much more intense and much more rapid than that in cats simply infected for the first time in the absence of specific antibodies (Pedersen N. and Boyle J., Am. J. Vet. Res. 1980, 41, 868–876; Weiss R. et al., Comp. Immunol. Microb. Infect. Dis. 1981, 4, 175–189; Weiss R. et al., Am. J. Vet. Res. 1980, 41, 663–671). It is thought that the binding of the antibody-virus immune complexes to the Fc receptors present at the surface of macrophages constitutes the mechanism which enhances the acceleration of the entry of the virus into the cells and its rapid diffusion in the body (Porterfield, J. Advances in Virus research, 1986, 31, 335–355; Weiss et al. 1981). This enhancement phenomenon has been observed among the coronaviruses only with the FIP virus.

The FIP virus comprises three structural proteins. The largest in size is the "SPIKE" or spicule (S) protein. This S protein is highly glycosylated and it is the one which induces in cats both neutralizing antibodies and enhancing antibodies. Studies carried out in vitro with neutralizing monoclonal antibodies directed against the FIP virus have shown that the major neutralizing epitopes are all situated on the S glycoprotein and that they correspond, to a large degree, to the epitopes involved in the enhancement phenomenon (Corapi W. et al., J. Virol. 1992, 66, 6695–6705; Olsen C. et al., J. Virol. 1992, 66, 956–965).

An effective vaccination against FIP should lead to the appearance of neutralizing antibodies without there being induction of enhancing antibodies. It has never been possible to develop such a vaccine up until now. The recombinant vaccines which do not contain the S glycoprotein can probably provide the best alternative for future FIP vaccines, but these antigens contribute only partially to the induction of the neutralizing response against the FIP virus. Of the three structural viral antigens, only the S glycoprotein is capable of inducing a substantial neutralizing response. Unfortunately, this glycoprotein also induces the concomitant appearance of enhancing antibodies. In spite of its importance in the induction of a good neutralizing response (and therefore in the protective response), the natural S glycoprotein appears to play an essential role in the FIP enhancement phenomenon and cannot therefore be used at the moment for the manufacture of vaccines meeting the criteria set out above.

The localization and characterization of the epitopes present on S and in particular those responsible for the neutralization and the enhancement is therefore necessary in order to determine the modifications to be made to the S glycoprotein (or to the gene which encodes this protein) in order to make it an effective immunogen for the vaccination of cats against FIP.

The nucleotide sequence and the protein sequence of the S glycoprotein of the FIP virus have been determined (de Groot R. et al. EP-A-0,264,979). This patent application does not teach how to identify the neutralizing epitopes and/or the enhancing epitopes on S. Neither does this document teach how to use the S sequence to manufacture a vaccine which is effective and nonenhancing against FIP.

Patent Application PCT WO-A-93/23421 claims the use of a truncated S glycoprotein or of a nucleic acid sequence encoding only a portion of S. In particular, the highly conserved region situated at the carboxy-terminal end of S (last 124 amino acids) is claimed for the preparation of a "universal" vaccine against coronaviruses. This document is very general and does not teach how to produce an FIP vaccine which does not induce enhancing antibodies in cats. The same is true of Patent Application PCT WO-A-93/23 422 which describes mixed constructs of FECV-FIPV chimeric S glycoprotein including the FIPV S fragments 542–597, 594–1454 or 651–1454.

Patent Application PCT WO-A-92/08487 claims the use of various peptides selected on the S proteins, or encoded by the S genes, of various FIPV virus strains, or by the FECV S gene sequence, for the diagnosis, treatment or prevention of FIP in cats. In particular, the 598–615 peptide of the S protein sequence of the FIPV virus strain 79-1146 is claimed for use in the form of a fusion protein with galactokinase, a recombinant protein capable of then being used for the diagnosis of anti-FIP antibodies in infected cats or as recombinant vaccine to induce protection against FIP in cats. Although envisaging variations in the sequences of the claimed peptides, this document does not teach precisely what the changes in the proposed sequences must be, and neither teaches how to produce a nonenhancing FIP vaccine, nor which of the S glycoprotein regions are involved in this phenomenon.

Patent Application GB-A-2,282,601, published after the priority date of the present application, proposes to produce a vaccine based on an S protein which is modified in order to avoid enhancement, by modification or deletion of at least one of the antigenic sites called D (corresponds to amino acids 496–524), A1 (corresponds to amino acids 531–555) and A2 (corresponds to amino acids 584–604), so as to make these sites antigenically inactive.

Great efforts have been made to identify the major antigenic sites present on the S proteins of the TGEV virus (Transmissible Gastro-Enteritis Virus) (Correa I. et al., J. Gen. Virol. 1990, 71, 271–279; Delmas B. et al., J. Gen. Virol. 1990, 71, 1313–1323), BCV (Bovine CoronaVirus) (Yoo D. et al., Virology 1991, 183, 91–98), MHV (Mouse Hepatitis Virus) (Takase-Yoden S. et al., Virus Res. 1990, 18, 99–108; Stuhler A. et al., J. Gen. Virol. 1991, 72, 1655–1658) and FIPV (Corapi W. et al., J. Virol. 1992, 66, 6695–6705; Olsen C. et al., J. Virol. 1992, 66, 956–965; Olsen C. et al., J. Gen. Virol. 1993, 74, 745–749). In all cases, multiple neutralizing domains were identified, and the immunodominant domains were generally localized on the S1 portion of the protein.

Studies relating specifically to the FIP virus have shown the existence on the S protein of epitopes which induce both a neutralizing response and an enhancing response with respect to infection with FIPV (Corapi W. et al., J. Virol. 1992, 66, 6695–6705; Olsen C. et al., J. Virol. 1992, 66, 956–965; Olsen C. et al., J. Gen. Virol. 1993, 74, 745–749). These same authors have shown that the neutralizing and enhancing monoclonal antibodies of anti-S specificity could be divided into 6 main groups according to their capacity to recognize different FIP virus strains and different mutants resistant to neutralization by these monoclonals ("mar" (monoclonal antibody resistant) mutants). However, the epitopes corresponding to the major antigenic regions on FIPV S have not been characterized. All the non- neutralizing monoclonal antibodies described by these authors (Olsen C. et al., J. Virol. 1992, 66, 956–965) are also nonenhancing in an in vitro enhancement test, which reinforces the hypothesis for a close relationship between neutralization and enhancement in the case of the FIP virus. The enhancement of viral infection by the antibodies occurs when the monocytes or macrophages are infected more effectively by the immune complexes, by a specific receptor-dependent endocytosis, than by the virus alone. In spite of all the studies performed on the antibody-dependent enhancement phenomenon, many questions remain unanswered. In particular, it is not known which specific viral components are responsible for the enhancement for each virus. Studies carried out up until now in FIPV indicate that the enhancement depends essentially on epitopes present on S (Olsen C. et al., 1993; Vennema H. et al., J. Virol. 1990, 64, 1407–1409).

Hohdatsu T. et al. (Arch. Virol. 1991, 120, 207–217) have found that anti-FIPV M monoclonal antibodies could induce an enhancement of the infection in vitro. This has not been confirmed in vivo by the studies performed with recombinants vaccinia/FIPV M and vaccinia/FIPV N. The immunization of cats with these two recombinants did not make it possible to observe an enhancement induced by either of these two proteins (Vennema H. et al. 1990). If M and N play a role in the enhancement, it is certainly at a level which is much lower than that played by S. During studies performed with the various viral systems where enhancement can be observed, a constant occurrence was observed: individual epitopes are capable of inducing both neutralizing antibodies and enhancing antibodies. This has been demonstrated for FIPV (Corapi W. et al., J. Virol. 1992, 66, 6695–6705; Olsen C. et al., J. Virol. 1992, 66, 956–965; Hohdatsu T. et al., Arch. Virol. 1991, 120, 207–217), for the dengue virus (Morens D. and Halstead S., J. Gen. Virol. 1990, 71, 2909–2917), and for HIV (Robinson W. Jr., J. Virol. 1991, 65, 4169–4176).

Recent results of the tests performed with experimental FIP vaccines appear to provide the most solid argument to date for the existence of a direct relationship between the enhancement observed in vitro and the accelerated disease in vivo in cats. The inoculation of cats with recombinants of the vaccinia virus expressing the S protein of the strain FIPV 79–1146 sensitizes the cats and induces after challenge an accelerated disease in the vaccinated cats compared with the nonvaccinated control cats (Vennema H. et al., J. Virol. 1990, 64, 1407–1409). The inoculation of vaccinia recombinants expressing either the M protein, or the N protein, need not predispose the cats to an accelerated disease. These in vivo results are to be taken in parallel with the in vitro results demonstrating a predominant localization of the enhancing epitopes on S (Corapi W. et al., J. Virol. 1992, 66, 6695–6705; Olsen C. et al., J. Virol. 1992, 66, 956–965). Furthermore, recent experiments performed in order to study the efficacy of another candidate vaccine for FIP have demonstrated a statistically significant association between the capacity of a cat serum to induce an enhancement in vitro and the development in the same cat of an accelerated disease (Olsen C., Vet. Microb. 1993, 36, 1–37).

DESCRIPTION OF THE INVENTION

The subject of the present invention is the characterization of the epitopes involved in the enhancement of the FIP virus infection. The precise knowledge of the molecular structures responsible for the enhancement mechanism makes it possible to design antigens which do not induce the appearance of enhancing antibodies. These antigens are the essential components of an effective FIP vaccine.

Surprisingly, it has been discovered, by analyzing the sequence of the S gene of mutant FIPV viruses resistant to neutralization with neutralizing and enhancing monoclonal antibodies, or resistant to monoclonal antibodies which are only neutralizing and not enhancing, that it was possible to sidestep the mechanism of induction of enhancement by the S glycoprotein. Two major antigenic sites have been characterized with the monoclonal antibodies studied: A1 and A2. These sites are both surprisingly situated in the same region of the S protein. It appears that the strongly neutralizing and enhancing antibodies recognize both sites at the same time. This information suggests that the simultaneous binding of the two epitopes by the same antibody plays a direct role in the enhancement. Indeed, in parallel with this first discovery, it has been discovered that the neutralizing, but not enhancing, antibodies recognize only the A2 site. Enhancement could therefore be due to a confirmational modification by the coming together of the two epitopes A1 and A2. The A2 region includes amino acids 637–662 on the protein sequence of S (De Groot R. et al., J. Gen. Virol. 1987, 68, 2639–2646). The hydrophilic nature of this region and the fact that the 3 monoclonal antibodies tested all recognize this small domain suggest that A2 is a dominant neutralizing epitope of the S protein. Moreover, the close homology observed between the A1 site and a portion of the Aa subsite identified on the TGEV S protein (Gebauer F. et al., Virology 1991, 183, 225–238) suggests that A1, which comprises amino acids 562–598 must also be an important neutralizing epitope for the FIPV virus.

The coming together or the simultaneous binding, by the same antibody, of the A1 and A2 sites is necessary in order to induce enhancement through antibodies.

The subject of the present invention is the modification, by genetic engineering, of the sequence of the FIPV S gene in the region of the A1 and/or A2 sites, in particular in order to modify at least one of both sites, preferably to modify the A1 site so that the protein expressed presents an epitope modified so that the protein no longer induces enhancing antibodies and/or the A2 site. The A1 region can be modified in various ways, by means well known to persons skilled in the art. The A1 or A2 sites can be modified independently or simultaneously.

The modification of the A2 site may consist in a modification, such as a complete deletion, leading to a loss of antigenicity of the site, but one preferes that, as for the A1 site, the modification expresses an epitope which is modified so that the protein no more induces enhancing antibodies.

The A1 region has a common part with the so-called "A2" region in patent application GB-A-2,282,601 (WO-A-95/

07987) cited above, but contrary to the invention it provides for mutations (modifications) or deletions which cause a loss of antigenicity of the modified or deleted region.

The subject of the invention is in particular a nucleotide sequence comprising the complete FIPV S gene, having at least one modification, preferably a mutation and/or limited deletion, in the antigenic A2 region which encodes amino acids 637 to 662 and/or in the antigenic A1 region which encodes amino acids 562 to 598, with the exception of total deletion or an important mutation or deletion having the same consequences than a total deletion, say a loss of antigenicity of the modified region.

The present application is now limited to that part of the invention which concerns the modifications which allow the suppression of the enhancing antibodies induction without modification of the antigenicity, at least for the A1 site.

Of course, the expression nucleotide sequence comprising the complete FIPV S gene covers the types 1 and 2 FIPV strains as well as the variants and the sequences which exhibit secondary variations, that is to say which do not affect the immunogenicity of the S protein, which also covers secondary mutations and deletions outside the A1 and A2 sites. Preferably ' the variations in the sequence must not modify the functionality of the S glycoprotein.

This therefore includes the sequences having a high degree of homology with the previous sequences, including when the degeneracy of the genetic code is taken into account, this homology being sufficiently high so that the expressed polypeptide makes it possible to induce an effective vaccinal protection.

Limited deletion is understood to mean preferably a point deletion (corresponding to 1 amino acid) or a microdeletion (up to 6 amino acids).

Mutations or deletions of the codons encoding the cysteines situated in A1 and A2 will be avoided in general.

In addition, mutations and secondly point deletions (except Cys) will be preferred to more extensive mutations and deletions.

For the A1 site, the modifications comprise a minima a mutation for at least one and, preferably, for both of the codons encoding Asp 568 and Asp 591 in order to have any other amino acid at these positions. Provided that amino acids 568 and 591 are not Asp, any other amino acid in the 562–598 region can be substituted for the natural amino acid in the position considered.

The modifications of the A1 site also comprise limited deletions of this region comprising amino acids 568 and/or 591.

For the A2 site, the modifications comprise a minima a mutation for at least one and, preferably, for the three codons encoding Asp 643, Arg 649 and Arg 656 in order to have any other amino acid at these positions. The modifications of the A2 site also comprise the total deletion/partial deletions of this region comprising amino acids 643, 649 and/or 656.

The subject of the present invention is also the use of the FIPV genes thus modified for the in vitro expression of recombinant FIPV S proteins and for the preparation of purified subunit vaccines for the vaccination of cats against FIP.

The subject of the present invention is also the use of the FIPV S genes thus modified for the construction of recombinant viral vectors expressing these modified genes. These viral vectors may be replicative or nonreplicative recombinant viruses and more particularly poxviruses (example: vaccinia virus and its derivatives, canarypox virus and the like), herpesviruses (in particular feline herpesvirus), or adenoviruses.

The subject of the present invention is the preparation of vaccines against FIP with these recombinant viruses.

The subject of the present invention is also the immunization of cats against FIP with plasmids containing the FIPV S genes, modified according to the present invention, and placed under the control of a strong promoter (for example HCMV IE, SV40, and the like) and of regulatory signals for transcription and translation. The plasmids are present in a vehicle capable of allowing direct injection into cats, especially via the intramuscular route. They are especially naked plasmids as described in International Patent Application WO 90/11092.

The subject of the present invention is finally the preparation of vaccines against FIP comprising one (or more) FIPV S protein(s), modified according to the present invention, preferably combined with other FIPV virus proteins such as for example the M protein.

Another vaccinal solution consists in using cells (in particular of feline origin) constitutively expressing the S glycoprotein according to the invention.

EXAMPLES

Example 1

Cloning and Expression of the Fragments of the FIPV S Gene

With the aim of localizing the region of the FIPV S gene responsible for the neutralization and for the enhancement, the cloning of overlapping fragments of the FIPV S gene was undertaken so as to express these fragments in the form of fusion proteins with the protein of gene 10 of the T7 phage. The oligonucleotide sequence for the amplification of the various fragments was chosen so as to cover the entire coding region of the S gene in the form of 3 large fragments of about 1600 base pairs (bp) and 12 smaller subfragments of about 400 to 500 bp. These oligonucleotides contain the BamHI, XbaI or XhoI restriction sites in order to facilitate their cloning. The reverse transcription of RNA and the amplification of the complementary DNA by the polymerase chain reaction were performed according to standard techniques (Sambrook J. et al., Molecular Cloning: a laboratory manual, 2nd ed., Cold Spring Harbor Laboratory, Cold Spring Harbor, N.Y.). The amplified DNA was digested with the appropriate enzymes and cloned into the vector pBluescript (Stratagene, La Jolla, Calif.).

The limits of the various fragments cloned from the S gene of strain 79–1146 of the FIPV virus are indicated below: (all the positions refer to the S gene sequence of the FIPV 79–1146 strain, published by De Groot R. et al. (J. Gen. Virol. 1987, 68, 2639–2646).

Fragment F1: nucleotides 70 to 1736.
Fragment F2: nucleotides 1519 to 3160.
Fragment F3: nucleotides 2773 to 4428.
Fragment S1: nucleotides 70–535.
Fragment S2: nucleotides 394–862.
Fragment S3: nucleotides 742–1221.
Fragment S4: nucleotides 1045–1539.
Fragment S5: nucleotides 1339–1734.
Fragment S6: nucleotides 1594–2089.
Fragment S7: nucleotides 1963–2443.
Fragment S8: nucleotides 2296–2838.
Fragment S9: nucleotides 2743–3004.
Fragment S10: nucleotides 2890–3506.
Fragment S11: nucleotides 3352–4063.
Fragment S12: nucleotides 3895–4428.

The various FIPV fragments cloned were then isolated from the Bluescript clones by NotI and XhoI digestion and then recloned into the vector PTOPE-SX for the transcription and translation stage in vitro.

The construction of pTOPE-SX is described below.

The plasmid pTOPE-1b(+) (Novagen) contains the T7 promoter and a portion of gene 10 of the T7 phage followed by a polylinker. This polylinker was completely removed by digestion with the restriction enzymes SacII and XhoI and replaced with the 82 bp SacII-XhoI fragment isolated from the polylinker contained in pBluescript. An additional nucleotide was added to this fragment so as to place all the FIPV fragments cloned into pBluescript in phase with the gene 10 phase. The new plasmid was called pTOPE-SX. The transcription and translation in vitro with the T7 phage RNA polymerase of the inserts contained in pTOPE-SX makes it possible to obtain fusion proteins containing 260 amino acids of the gene 10 protein followed by the amino acids encoded by the FIPV inserts.

Example 2

Recognition of the FIPV S Peptides by Monoclonal Antibodies

With the aim of localizing the general region of the FIPV virus S gene responsible for neutralization and enhancement, overlapping fragments of this gene were cloned by PCR into the vector pBluescript in the form of three large fragments (F1, F2 and F3; FIG. 1) and 12 small subfragments (S1 to S12). These FIPV inserts were then subcloned into the vector pTOPE-SX for their transcription and their translation in vitro.

The coupled transcription and translation reactions in vitro were performed using the "TNT Reticulocyte Lysate" system (Promega, Madison, Wis.) according to the technique recommended by the manufacturer, in the presence of $^{35}$S-methionine (Amersham France). To study the effect of the post-translational processing of the proteins, the reactions were also performed in the presence of dog pancreatic microsomal membranes (Promega). The translational products were separated by SDS-polyacrylamide gel electrophoresis and visualized by autoradiography.

The radioimmunoprecipitation assays (RIPA) were performed by mixing 5 μl of the fusion protein translation mixture with 5 μl of cat serum or monoclonal antibody in 200 μl of TNE Triton X-100 buffer (NaCl 150 mM, Tris (pH 8.0) 50 mM, EDTA 5 mM, Triton X-100 0.1%) and by stirring this mixture at +4° C. for 1 hour. Cat sera which were positive and negative for FIPV as well as a monoclonal directed against the first 10 amino acids of the T7 gene 10 protein (T7 Tag monoclonal antibody, Novagen) were used as controls. The immune complexes are adsorbed by addition of 50 μl of an agarose-recombinant G protein conjugate (Boehringer Mannheim, Mannheim, Germany) to the samples containing the monoclonal antibodies or by addition of 50 μl of an agarose-recombinant A protein conjugate (Boehringer Mannheim) to the samples containing the cat sera. The agarose-bound immune complexes were centrifuged for 30 s and washed twice with RIPA buffer (150 mM NaCl, 50 mM Tris (pH 8.0), 1% Triton X-100, 0.5% sodium deoxycholate, 0.1% SDS) and once with Tris-Triton buffer (10 mM Tris (pH 8.0), 0.1% Triton X-100). The centrifuged samples are then separated by electrophoresis. The gels are fixed and treated with an Amplify solution (Amersham) and visualized by autoradiography.

The large fragments F1, F2 and F3 have a size of about 62 kDa, which gives fusion proteins of about 90 kDa, effectively corresponding to the sizes observed. The small fragments S1 to S12 are about 18 kDa in size, which gives fusion proteins of about 46 kDa.

In order to optimize the conditions for recognizing the FIPV S fusion peptides by the monoclonal antibodies, the fusion proteins were also translated in the presence of dog pancreas microsomal membranes. The glycosylation of the N-terminal end of S (fragment F1) results in a change in the size of the fusion protein F1 from 90 kDa to 98 kDa or 145 kDa, corresponding to an increase of 8 or of 55 kDa respectively. An increase of 8 kDa is also observed for the size of the subfragment S1 which passes from 48 to 54 kDa. The size of the other FIPV S fragments is not modified by the translation performed in the presence of microsomal membranes.

The specific anti-FIPV S monoclonal antibodies 23F4.5, 24H5.4 and 18A7.4 (Corapi W. et al., J. Virol. 1992, 66, 6695–6705) recognize the fragment F2 and the subfragment S6 which have a sequence of 165 amino acids in common (positions 509 to 673 on the sequence of the S protein of strain 79–1146 (De Groot R. et al., J. Gen. Virol. 1987, 68, 2639–2646). The recognition of the fragment F2 is not improved by the use of proteins translated in the presence of microsomal membranes, which suggests that glycosylation is not necessary for the recognition of the epitopes investigated.

Example 3

Sequencing of the Mutant Viruses Resistant to Neutralization With the Anti-FIPV S Monoclonal Antibodies ("mar" mutants)

In order to localize the antigenic sites localized on fragment S6, the S6 region of several mar FIPV mutants was amplified by PCR and cloned into the vector pBluescript SK+ and sequenced. The sequence of the mar mutants was established on the independent mar mutants obtained with the same monoclonal as well as with clones obtained from independent PCR amplifications with the same mar mutant. The sequence of each clone was established on both strands using the Sequenase kit (Amersham) according to the technique recommended by the manufacturer.

The sequences obtained were compared with the homologous sequence of the parental virus 79–1146. The mar mutants analyzed are the mutants identified as mar 23F4.5, mar 18A7.4 and mar 24H5.4. These mutants were obtained with the monoclonal antibodies 23F4.5, 18A7.4 and 24H5.4 respectively, described by C. Olsen (Olsen C. et al., J. Virology 1992, 66, 956–965) and W. Corapi (Corapi W. et al., J. Virology 1992, 66, 6695–6705).

The monoclonal 23F4.5 has a neutralizing titre of 20480 (Corapi, 1992) and induces an enhancement of the infection in vitro which is at least 100 times the normal level (Olsen, 1992). The mutant mar 23F4.5 has mutations at positions 1840 and 2014 which induce amino acid changes in the sequence of the S protein for residues 591 (Asp → Tyr) and 649 (Arg → Gly). The monoclonal 18A7.4 has a neutralizing titre of 5120 and induces an enhancement of the infection in vitro which is at least 100 times the normal level. The mutant mar 18A7.4 has mutations at positions 1772 and 2036 which induce amino acid changes for residues 568 (Asp → Val) and 656 (Arg → Lys).

The monoclonal 24H5.4 has a neutralizing titre of 96 and it has the characteristic of not inducing enhancement of the infection (Olsen, 1992). The mutant mar 24H5.4 has only one mutation at position 1996 which induces an amino acid change for residue 643 (Asp → Tyr).

Example 4

Mutagenesis of the A1 Site

The central fragment of the 1723 bp HindIII—HindIII FIPV S gene (nucleotides 1696 to 3418) is cloned into the vector pBS-SK+ to give the plasmid pFIPV-S2. The A1 site is situated on the HindIII-SspI subfragment (positions 1696 to 1845) of this fragment. The A1 site is mutagenized by PCR using the following strategy:

OLIGO A11 (95 mer) (SEQ ID NO: 1) =

5' ATGAAGCTTAGTGGTTATGGTCAACCCATAGCCTCGACACTAAGTAACATCACA-
CTACCAATGCAGGATAACAATACTGTTGTGTACTGTATTCG 3'

OLIGO A12 (88 mer) (SEQ ID NO. 2) =

5' AAAAATATTGTACCATAAAGAACTTTTGCAAGTGGAATGAACATAAACTGAGAA-
TTGGTTAGAACGAATACAGTACACAACAGTATTG 3'

OLIGO A13 (20 mer) (SEQ ID NO: 3) =

5' ATGAAGCTTAGTGGTTATGG 3'

OLIGO A14 (20 mer) (SEQ ID NO: 4) =

5' AAAAATATTGTACCATAAAG 3'

The oligonucleotides A11 and A12 are hybridized with each other by means of their common complementary sequence of 23 base pairs. The hybrid thus obtained then serves, after elongation of its 3' ends, as template for a PCR reaction using the oligonucleotides A13 and A14. This PCR amplification reaction makes it possible to obtain a 159 bp fragment. This fragment is then digested with the restriction enzymes HindIII and SspI to produce a 149 bp HindIII-SspI fragment (fragment A). This fragment contains the A1 site modified at two positions (Val instead of Asp at position 568 and Tyr instead of Asp at position 591). The plasmid pFIPV-S2 is digested with HindIII and partially digested with SspI so as to isolate the 1569 bp SspI-HindIII fragment (fragment B) by Geneclean (BIO101 Inc., La Jolla, Calif.). The vector pBS-SK+ is digested with HindIII and dephosphorylated so as to produce fragment C (2960 bp).

The fragments A, B and C are then ligated together so as to produce the plasmid pFIPSA1*. This plasmid contains the HindIII—HindIII fragment of the FIPV S gene modified with respect to two amino acids of the A1 site.

The FIPV S gene is then reconstituted by replacing, simply by cloning, the natural HindIII—HindIII fragment (positions 1696 to 3418) with the HindIII—HindIII fragment contained in the plasmid PFIPSA1*. The complete FIPV S gene modified at the A1 site can then be used for the constructions of expression plasmids or of recombinant viruses.

Example 5

Mutagenesis of the A2 Site

OLIGO A21 (20 mer) (SEQ ID NO: 5) =

5' GGACAATATTTTTAATCAAG 3'

OLIGO A22 (36 mer) (SEQ ID NO: 6)

5' TTTAACAACCTGCTCATTGGTTCCTGTACGTGCAGC 3'

OLIGO A23 (36 mer) (SEQ ID NO: 7) =

5' AAGTTTTATGTTGCTGCACGTACAGGAACCAATGAG 3'

OLIGO A24 (20 mer) (SEQ ID NO: 8) =

5' ATCACTAACATTTTTAAAGC 3'

A PCR reaction (PCR A) is performed with the oligonucleotides A21 and A22 and with the plasmid pFIPV-S2 as template so as to synthesize a PCR fragment of 199 bp (fragment A).

A PCR reaction (PCR B) is performed with the oligonucleotides A23 and A24 and with the plasmid pFIPV-S2 as template so as to give a PCR fragment of 273 bp (fragment B).

The fragments PCR A and B are hybridized with each other by means of their complementary region of 46 bp and the product of this hybridization, after extension of the 3' ends, is amplified by a PCR reaction (PCR C) with the oligonucleotides A21 and A24 so as to give a PCR fragment of 424 bp. This PCR fragment is then digested with SspI and DraI so as to give the SspI-DraI restriction fragment of 402 bp (fragment C).

The plasmid pFIPV-S2 is digested with HindIII and SspI so as to isolate the HindIII-SspI fragment of 149 bp (fragment D).

The plasmid pFIPV-S2 is digested with HindIII and DraI so as to isolate the DraI-HindIII restriction fragment of 1170 bp (fragment E). The vector pBS-SK+ is digested with HindIII and dephosphorylated so as to give the fragment F (2960 bp).

Fragments C, D, E and F are ligated together so as to give the plasmid pFIPSA2*. The 1723 bp central HindIII—HindIII fragment of the FIPV S gene contained in pFIPSA2* has an A2 site which is modified at 3 amino acids (Tyr instead of Asp at position 643, Gly instead of Arg at position 649, and Lys instead of Arg at position 656).

The FIPV S gene is then reconstituted by replacing, simply by cloning, the natural HindIII—HindIII fragment (positions 1696 to 3418) with the HindIII—HindIII fragment contained in the plasmid pFIPSA2*. The complete FIPV S gene modified at the A2 site can then be used for the constructions of expression plasmids or of recombinant viruses.

Example 6

Mutagenesis of the A1 and A2 Sites.

Fragments A (Example 4), C and E (Example 5) are ligated with the vector pBS-SK+, previously digested with HindIII and dephosphorylated, so as to give the plasmid pFIPSA1*A2*. The 1723 bp central HindIII—HindIII fragment of the FIPV S gene contained in pFIPSA1*A2* has 2 amino acid changes at the A1 site (see Example 4) and 3 amino acid changes at the A2 site (see Example 5).

The FIPV S gene is then reconstituted by replacing, simply by cloning, the natural HindIII—HindIII fragment with the 1723 bp HindIII—HindIII fragment contained in pFIPSA1*A2*. The complete FIPV S gene comprising modifications at the A1 and A2 sites can then be used for the construction of expression plasmids or of recombinant viruses.

Example 7

Construction of Deletions at the A1 and A2 Sites.

Based on the cloning strategy described above (mutagenesis using PCR reactions), deletions which preserve the reading frame of the FIPV S gene can be introduced at the A1 and/or A2 sites. Based on the same scheme as described above (see Example 6), a central HindIII—HindIII fragment of the FIPV S gene can be constructed which has a deletion in the A1 site and/or a deletion in the A2 site.

What is claimed:

1. An isolated nucleotide sequence of the infectious peritonitis virus (FIPV) S gene having the nucleotide sequence of the 79-1146 FIPV strain modified in a codon selected from the group consisting of:

(i) the codon coding for Asp at position 568;
   (ii) the codon coding for Asp at position 591;
   (iii) the codon coding for Asp at position 643;
   (iv) the codon coding for Arg at position 649; and
   (v) the codon coding for Arg at position 656 or a combination thereof;

said modifications being such that the modified S protein expressed by said modified sequence no longer recognizes enhancing antibodies.

2. The isolated nucleotide sequence according to claim 1, wherein the codon modified is the codon coding for Asp at position 568.

3. The isolated nucleotide sequence according to claim 1, wherein the codon modified is the codon coding for Asp at position 591.

4. The isolated nucleotide sequence according to claim 1, wherein the codon modified is the codon coding for Asp at position 643.

5. The isolated nucleotide sequence according to claim 1, wherein the codon modified is the codon coding for Arg at position 649.

6. The isolated nucleotide sequence according to claim 1, wherein the codon modified is the codon coding for Arg at position 656.

7. An isolated nucleotide sequence of FIPV S gene having the nucleotide sequence of the 79-1146 feline infectious peritonitis virus (FIPV) strain according to claim 1 modified in two, three, four, or five of codons (i) to (v).

8. A purified preparation of the modified S polypeptide expressed by the sequence according to claim 1.

* * * * *

UNITED STATES PATENT AND TRADEMARK OFFICE
CERTIFICATE OF CORRECTION

Page 1 of 1

PATENT NO.   : 6,080,850
DATED        : June 27, 2000
INVENTOR(S)  : Darteil et al.

It is certified that error appears in the above-identified patent and that said Letters Patent is hereby corrected as shown below:

Line [73], change "Rhone Merieux" to --Merial--.

Signed and Sealed this

Tenth Day of July, 2001

Attest:

NICHOLAS P. GODICI
Attesting Officer
Acting Director of the United States Patent and Trademark Office

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 95 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

ATGAAGCTTA GTGGTTATGG TCAACCCATA GCCTCGACAC TAAGTAACAT CACACTACCA    60

ATGCAGGATA ACAATACTGT TGTGTACTGT ATTCG    95

(2) INFORMATION FOR SEQ ID NO:2:

(i) SEQUENCE CHARACTERISTICS:
      (A) LENGTH: 88 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

AAAAATATTG TACCATAAAG AACTTTTGCA AGTGGAATGA ACATAAACTG AGAATTGGTT    60

AGAACGAATA CAGTACACAA CAGTATTG    88

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

ATGAAGCTTA GTGGTTATGG                                                      20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

AAAAATATTG TACCATAAAG                                                      20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

GGACAATATT TTTAATCAAG                                                      20

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

TTTAACAACC TGCTCATTGG TTCCTGTACG TGCAGC                                    36

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
AAGTTTTATG TTGCTGCACG TACAGGAACC AATGAG                                    36

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

ATCACTAACA TTTTTAAAGC                                                      20
```